US012661491B2

(12) United States Patent
Balji et al.

(10) Patent No.: US 12,661,491 B2
(45) Date of Patent: Jun. 23, 2026

(54) SENSOR ASSEMBLY AND SYSTEM, METHOD, AND COMPUTER PROGRAM PRODUCT FOR IDENTIFYING DEVICES CONNECTED TO DEVICE CONNECTORS

(71) Applicant: Becton, Dickinson and Company, Franklin Lakes, NJ (US)

(72) Inventors: Jack Balji, Mahwah, NJ (US); Mark Andrew Nelson, Harrison, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 660 days.

(21) Appl. No.: 17/172,211

(22) Filed: Feb. 10, 2021

(65) Prior Publication Data

US 2021/0244932 A1 Aug. 12, 2021

Related U.S. Application Data

(60) Provisional application No. 62/975,430, filed on Feb. 12, 2020.

(51) Int. Cl.
| | |
|---|---|
| *A61M 39/10* | (2006.01) |
| *A61M 5/31* | (2006.01) |

(Continued)

(52) U.S. Cl.
CPC .............. *A61M 39/10* (2013.01); *A61M 5/31* (2013.01); *A61M 25/00* (2013.01); *A61M 39/16* (2013.01);

(Continued)

(58) Field of Classification Search
CPC ........ A61M 39/10; A61M 5/31; A61M 25/00; A61M 39/16; A61M 39/20;

(Continued)

(56) References Cited

U.S. PATENT DOCUMENTS

| | | | |
|---|---|---|---|
| 5,520,653 | A | 5/1996 | Reilly et al. |
| 10,166,327 | B2 | 1/2019 | Tieck et al. |

(Continued)

FOREIGN PATENT DOCUMENTS

| | | |
|---|---|---|
| JP | 2013534163 A | 9/2013 |
| JP | 2017506530 A | 3/2017 |

(Continued)

OTHER PUBLICATIONS

Interlink Electronics Sensor Technologies, FSR 402 Data Sheet, FSR 400 Series Round Force Sensing Resistor, 4 pages.

*Primary Examiner* — Lauren P Farrar
(74) *Attorney, Agent, or Firm* — The Webb Law Firm

(57) ABSTRACT

A sensor assembly may include a sensor surrounding a connector of a medical device. The sensor may be configured to detect a dimension of an end of another connector of another medical device when the another connector of the another medical device is connected to the connector of the medical device. A system may include the sensor assembly and one or more processors programmed and/or configured to determine a type of the another medical device based on the detected dimension. A method may include detecting, with a sensor surrounding a connector of a medical device, a dimension of an end of another connector of another medical device when the another connector of the another medical device is connected to the connector of the medical device; and determining a type of the another medical device based on the detected dimension.

24 Claims, 9 Drawing Sheets

(51) Int. Cl.

| | |
|---|---|
| *A61M 25/00* | (2006.01) |
| *A61M 39/16* | (2006.01) |
| *A61M 39/20* | (2006.01) |
| *G16H 40/67* | (2018.01) |

(52) U.S. Cl.
CPC ............ *A61M 39/20* (2013.01); *G16H 40/67* (2018.01); *A61M 2205/3306* (2013.01); *A61M 2205/332* (2013.01); *A61M 2205/3337* (2013.01); *A61M 2205/3576* (2013.01); *A61M 2205/50* (2013.01); *A61M 2205/581* (2013.01); *A61M 2205/583* (2013.01)

(58) Field of Classification Search
CPC .... A61M 2205/3306; A61M 2205/332; A61M 2205/3337; A61M 2205/3576; A61M 2205/50; A61M 2205/581; A61M 2205/583
See application file for complete search history.

(56) References Cited

U.S. PATENT DOCUMENTS

| | | | | |
|---|---|---|---|---|
| 2006/0087325 | A1* | 4/2006 | Ariav ................... | A61B 5/6838 |
| | | | | 324/637 |
| 2008/0012049 | A1* | 1/2008 | Niwa ................... | G01N 27/414 |
| | | | | 257/253 |
| 2012/0203185 | A1 | 8/2012 | Kristensen et al. | |
| 2013/0113057 | A1 | 5/2013 | Taylor | |
| 2013/0221097 | A1* | 8/2013 | Day ........................ | A61M 5/20 |
| | | | | 235/437 |
| 2015/0306365 | A1* | 10/2015 | Besko ................... | A61M 39/10 |
| | | | | 604/111 |
| 2016/0015886 | A1* | 1/2016 | Pananen ............. | A61M 5/1413 |
| | | | | 604/111 |
| 2017/0065763 | A1* | 3/2017 | Rossitto ............ | A61M 5/14546 |
| 2019/0070402 | A1* | 3/2019 | Isaacson ............... | A61M 39/10 |
| 2021/0100996 | A1* | 4/2021 | Wijesuriya ............ | A61M 39/12 |

FOREIGN PATENT DOCUMENTS

| | | |
|---|---|---|
| JP | 2017521186 A | 8/2017 |
| WO | 2019050683 A1 | 3/2019 |

* cited by examiner

SENSOR ASSEMBLY AND SYSTEM, METHOD, AND COMPUTER PROGRAM PRODUCT FOR IDENTIFYING DEVICES CONNECTED TO DEVICE CONNECTORS

CROSS-REFERENCE TO RELATED APPLICATION

The present application claims priority to U.S. Provisional Application Ser. No. 62/975,430, entitled "Sensor Assembly and System, Method, and Computer Program Product for Identifying Devices Connected to Device Connectors", filed Feb. 12, 2020, the entire disclosure of which is hereby incorporated by reference in its entirety.

BACKGROUND

1. Field

The present disclosure relates generally to identifying devices and, in some non-limiting embodiments or aspects, to systems, devices, products, apparatus, and/or methods for identifying devices that are being or have been connected to device connectors.

2. Technical Considerations

Existing systems in the medical field may detect when two devices are connected with each other by employing RFID technology or electrical connections between the two devices. However, these existing systems may not identify a type of medical device that is connected without detecting identification numbers of the medical devices. For example, RFID tags may store identification numbers or barcode readers may be used to read barcodes including the identification numbers associated with medical devices. In this way, communications between devices, readers, and/or tags may be needed and/or medical devices without RFID tags or barcodes (or with incompatible tags or barcodes) may not be identified. Accordingly, there is a need in the art for improving identification of devices connected to device connectors.

SUMMARY

Accordingly, provided are improved systems, devices, products, apparatus, and/or methods for identifying devices connected to device connectors.

According to some non-limiting embodiments or aspects, provided is a sensor assembly including: a sensor surrounding a connector of a medical device, wherein the sensor is configured to detect a dimension of an end of another connector of another medical device when the another connector of the another medical device is connected to the connector of the medical device.

According to some non-limiting embodiments or aspects, provided is a system including: a sensor surrounding a connector of a medical device, wherein the sensor is configured to detect a dimension of an end of another connector of another medical device when the another connector of the another medical device is connected to the connector of the medical device; and one or more processors programmed and/or configured to determine a type of the another medical device based on the detected dimension.

According to some non-limiting embodiments or aspects, provided is a method including: detecting, with a sensor surrounding a connector of a medical device, a dimension of an end of another connector of another medical device when the another connector of the another medical device is connected to the connector of the medical device; and determining, with at least one processor, a type of the another medical device based on the detected dimension.

According to some non-limiting embodiments or aspects, provided is a computer program product including at least one non-transitory computer-readable medium including program instructions that, when executed by at least one processor, cause the at least on processor to: control a sensor surrounding a connector of a medical device to detect a dimension of an end of another connector of another medical device when the another connector of the another medical device is connected to the connector of the medical device; and determine a type of the another medical device based on the detected dimension.

Further embodiments or aspects are set forth in the following numbered clauses:

Clause 1. A sensor assembly comprising: a sensor surrounding a connector of a medical device, wherein the sensor is configured to detect a dimension of an end of another connector of another medical device when the another connector of the another medical device is connected to the connector of the medical device.

Clause 2. The sensor assembly of clause 1, wherein the sensor includes a force sensor.

Clause 3. The sensor assembly of any of clauses 1 and 2, wherein the force sensor includes a plurality of switches arranged at different distances from a center of the connector of the medical device, and wherein each switch of the plurality of switches is configured to be actuated in response to a physical force applied to that switch.

Clause 4. The sensor assembly of any of clauses 1-3, wherein the plurality of switches includes a plurality of conductive circuits surrounding the connector of the medical device.

Clause 5. The sensor assembly of any of clauses 1-4, wherein the plurality of conductive circuits includes a plurality of concentric rings.

Clause 6. The sensor assembly of any of clauses 1-5, wherein the plurality of switches includes a flexible layer of conductive or semi-conductive material on the plurality of conductive circuits.

Clause 7. The sensor assembly of any of clauses 1-6, wherein the flexible layer of conductive or semi-conductive material includes a force-sensing resistor or a carbon and/or graphite infused polymer.

Clause 8. The sensor assembly of any of clauses 1-7, wherein the plurality of switches includes a water-impermeable coating surrounding the flexible layer and the plurality of conductive circuits.

Clause 9. The sensor assembly of any of clauses 1-8, wherein the plurality of switches includes a layer of anisotropic elastic material on the flexible layer.

Clause 10. The sensor assembly of any of clauses 1-9, wherein the plurality of switches includes a spring loaded metallic ring on the plurality of conductive circuits.

Clause 11. The sensor assembly of any of clauses 1-10, wherein the sensor includes an optical sensor.

Clause 12. The sensor assembly of any of clauses 1-11, wherein the sensor is removably attached to the connector of the medical device.

Clause 13. The sensor assembly of any of clauses 1-12, wherein the sensor is integrally formed with the connector of the medical device.

Clause 14. The sensor assembly of any of clauses 1-13 wherein the connector includes a needless connector or a Luer connector.

Clause 15. The sensor assembly of any of clauses 1-14, wherein the detected dimension includes at least one of (i) a distance of an outer edge of the end of the another connector of the another medical device from a center of the connector of the medical device and (ii) a cross sectional area of the end of the another connector of the another medical device.

Clause 16. The sensor assembly of any of clauses 1-15, further comprising: an indicator configured to provide at least one of an audio indication and a visual indication associated with the dimension of the end of the another connector of the another medical device.

Clause 17. The sensor assembly of any of clauses 1-16, further comprising: a wireless communication device configured to communicate, to a remote computing device, information associated with at least one of (i) the dimension of the end of the another connector of the another medical device and (ii) a connection or a disconnection of the medical device to or from the another medical device.

Clause 18. The sensor assembly of any of clauses 1-17, further comprising: one or more processors programmed and/or configured to determine a type of the another medical device based on the detected dimension.

Clause 19. A system comprising: a sensor surrounding a connector of a medical device, wherein the sensor is configured to detect a dimension of an end of another connector of another medical device when the another connector of the another medical device is connected to the connector of the medical device; and one or more processors programmed and/or configured to determine a type of the another medical device based on the detected dimension.

Clause 20. The system of clause 19, wherein the sensor includes a force sensor, wherein the force sensor includes a plurality of switches arranged at different distances from a center of the connector of the medical device, wherein each switch of the plurality of switches is configured to be actuated in response to a physical force applied to that switch, and wherein actuation of a furthest switch of the plurality of switches from the center of the connector of the medical device is associated with the dimension of the end of the another connector of the another medical device.

Clause 21. The system of any of clauses 19 and 20, wherein the sensor includes an optical sensor, and wherein the detected dimension includes at least one of (i) a distance of an outer edge of the end of the another connector of the another medical device from a center of the connector of the medical device and (ii) a cross sectional area of the end of the another connector of the another medical device.

Clause 22. The system of any of clauses 19-21, further comprising: a wireless communication device configured to communicate, to the one or more processors, information associated with at least one of (i) the dimension of the end of the another connector of the another medical device and (ii) a connection or a disconnection of the medical device to or from the another medical device.

Clause 23. The system of any of clauses 19-22, wherein the type of the another medical device includes a syringe, a catheter, or a disinfecting cap.

Clause 24. A method comprising: detecting, with a sensor surrounding a connector of a medical device, a dimension of an end of another connector of another medical device when the another connector of the another medical device is connected to the connector of the medical device; and determining, with at least one processor, a type of the another medical device based on the detected dimension.

Clause 25. The method of clause 24, wherein detecting the dimension of the end of the another connector of the another medical device includes detecting at least one of (i) a distance of an outer edge of the end of the another connector of the another medical device from a center of the connector of the medical device and (ii) a cross sectional area of the end of the another connector of the another medical device.

Clause 26. The method of any of clauses 24 and 25, further comprising: providing, with an indicator, at least one of an audio indication and a visual indication associated with the dimension of the end of the another connector of the another medical device.

Clause 27. The method of any of clauses 24-26, further comprising: communicating, with a wireless communication device, to a remote computing device, information associated with at least one of (i) the dimension of the end of the another connector of the another medical device and (ii) a connection or a disconnection of the medical device to or from the another medical device.

Clause 28. The method of any of clauses 24-27, further comprising: controlling, with at least one processor, a flow of a fluid in a fluid flow path including the medical device and the another medical device based on the information.

Clause 29. A computer program product comprising at least one non-transitory computer-readable medium including program instructions that, when executed by at least one processor, cause the at least on processor to: control a sensor surrounding a connector of a medical device to detect a dimension of an end of another connector of another medical device when the another connector of the another medical device is connected to the connector of the medical device; and determine a type of the another medical device based on the detected dimension.

Clause 30. The computer program product of clause 29, wherein the instructions further cause the at least one processor to: control an indicator to provide at least one of an audio indication and a visual indication associated with the dimension of the end of the another connector of the another medical device.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of limits. As used in the specification and the claims, the singular form of "a," "an," and "the" include plural referents unless the context clearly dictates otherwise.

BRIEF DESCRIPTION OF THE DRAWINGS

Additional advantages and details of embodiments or aspects of the present disclosure are explained in greater detail below with reference to the exemplary embodiments that are illustrated in the accompanying schematic figures, in which.

DETAILED DESCRIPTION

Figure 1:
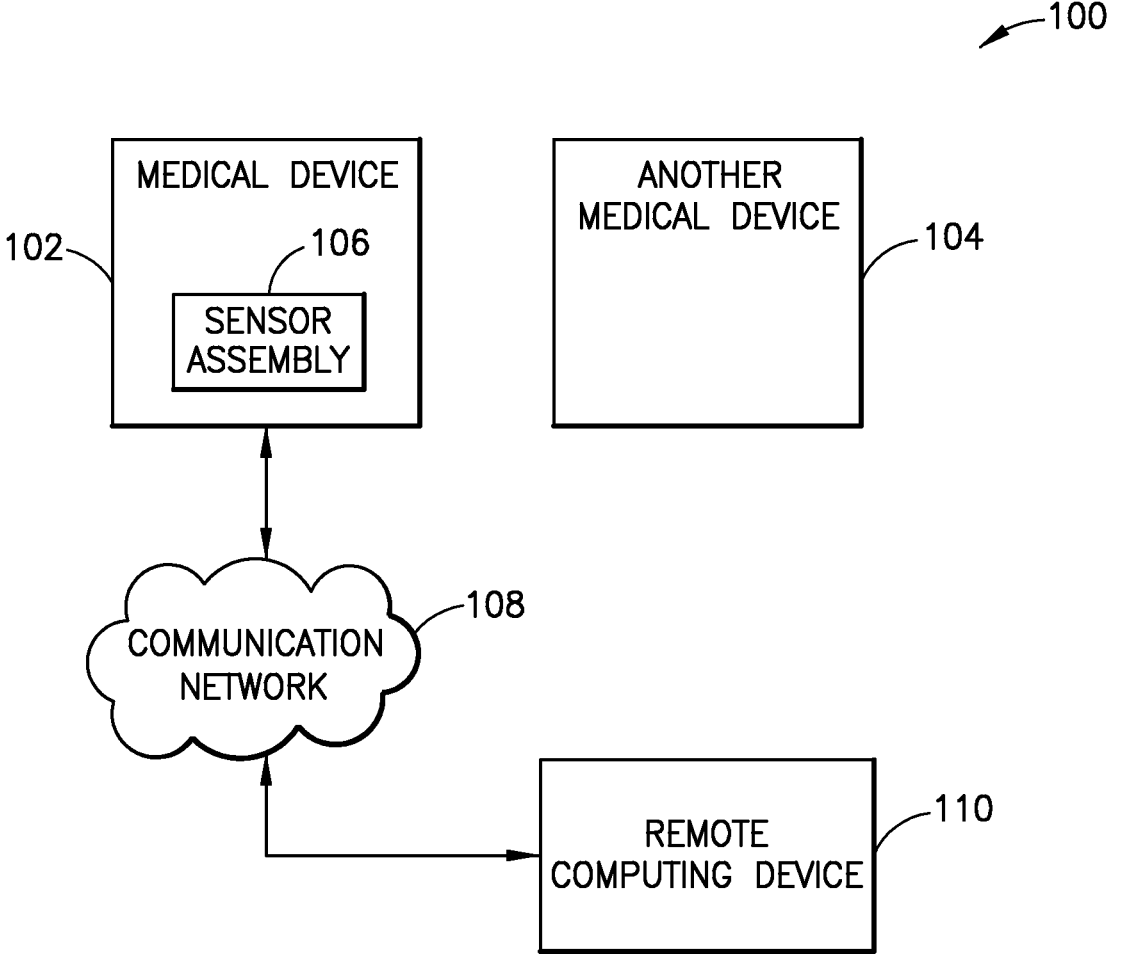
FIG. 1 is a diagram of non-limiting embodiments or aspects of an environment in which systems, devices, products, apparatus, and/or methods, described herein, may be implemented.

It is to be understood that the present disclosure may assume various alternative variations and step sequences, except where expressly specified to the contrary. It is also to be understood that the specific devices and processes illustrated in the attached drawings, and described in the following specification, are simply exemplary and non-limiting embodiments or aspects. Hence, specific dimensions and other physical characteristics related to the embodiments or aspects disclosed herein are not to be considered as limiting.

For purposes of the description hereinafter, the terms "end," "upper," "lower," "right," "left," "vertical," "horizontal," "top," "bottom," "lateral," "longitudinal," and derivatives thereof shall relate to the present disclosure as it is oriented in the drawing figures. However, it is to be understood that the present disclosure may assume various alternative variations and step sequences, except where expressly specified to the contrary. It is also to be understood that the specific devices and processes illustrated in the attached drawings, and described in the following specification, are simply exemplary embodiments or aspects of the present disclosure. Hence, specific dimensions and other physical characteristics related to the embodiments or aspects of the embodiments disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one." Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least in partially on" unless explicitly stated otherwise.

As used herein, the terms "communication" and "communicate" refer to the receipt or transfer of one or more signals, messages, commands, or other type of data. For one unit (e.g., any device, system, or component thereof) to be in communication with another unit means that the one unit is able to directly or indirectly receive data from and/or transmit data to the other unit. This may refer to a direct or indirect connection that is wired and/or wireless in nature. Additionally, two units may be in communication with each other even though the data transmitted may be modified, processed, relayed, and/or routed between the first and second unit. For example, a first unit may be in communication with a second unit even though the first unit passively receives data and does not actively transmit data to the second unit. As another example, a first unit may be in communication with a second unit if an intermediary unit processes data from one unit and transmits processed data to the second unit. It will be appreciated that numerous other arrangements are possible.

It will be apparent that systems and/or methods, described herein, can be implemented in different forms of hardware, software, or a combination of hardware and software. The actual specialized control hardware or software code used to implement these systems and/or methods is not limiting of the implementations. Thus, the operation and behavior of the systems and/or methods are described herein without reference to specific software code, it being understood that software and hardware can be designed to implement the systems and/or methods based on the description herein.

Some non-limiting embodiments or aspects are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

As used herein, the term "computing device" or "computer device" may refer to one or more electronic devices that are configured to directly or indirectly communicate with or over one or more networks. The computing device may be a mobile device, a desktop computer, or the like. Furthermore, the term "computer" may refer to any computing device that includes the necessary components to receive, process, and output data, and normally includes a display, a processor, a memory, an input device, and a network interface. An "application" or "application program interface" (API) refers to computer code or other data sorted on a computer-readable medium that may be executed by a processor to facilitate the interaction between software components, such as a client-side front-end and/or server-side back-end for receiving data from the client. An "interface" refers to a generated display, such as one or more graphical user interfaces (GUIs) with which a user may interact, either directly or indirectly (e.g., through a keyboard, mouse, touchscreen, etc.).

As used herein, the term "server" may refer to or include one or more processors or computers, storage devices, or similar computer arrangements that are operated by or facilitate communication and processing for multiple parties in a network environment, such as the Internet, although it will be appreciated that communication may be facilitated over one or more public or private network environments and that various other arrangements are possible. Further, multiple computers, e.g., servers, or other computerized devices, such as POS devices, directly or indirectly communicating in the network environment may constitute a "system," such as a merchant's POS system. As used herein, the term "data center" may include one or more servers, or other computing devices, and/or databases.

As used herein, the term "mobile device" may refer to one or more portable electronic devices configured to communicate with one or more networks. As an example, a mobile device may include a cellular phone (e.g., a smartphone or standard cellular phone), a portable computer (e.g., a tablet computer, a laptop computer, etc.), a wearable device (e.g., a watch, pair of glasses, lens, clothing, and/or the like), a personal digital assistant (PDA), and/or other like devices. The terms "client device" and "user device," as used herein, refer to any electronic device that is configured to communicate with one or more servers or remote devices and/or systems. A client device or user device may include a mobile device, a network-enabled appliance (e.g., a network-enabled television, refrigerator, thermostat, and/or the like), a computer, and/or any other device or system capable of communicating with a network.

As used herein, the term "application" or "application program interface" (API) refers to computer code, a set of rules, or other data sorted on a computer-readable medium that may be executed by a processor to facilitate interaction between software components, such as a client-side front-end and/or server-side back-end for receiving data from the client. An "interface" refers to a generated display, such as one or more graphical user interfaces (GUIs) with which a user may interact, either directly or indirectly (e.g., through a keyboard, mouse, etc.).

Non-limiting embodiments or aspects of the present disclosure are directed to a sensor assembly including a sensor surrounding a connector of a medical device, wherein the sensor is configured to detect a dimension of an end of another connector of another medical device when the another connector of the another medical device is connected to the connector of the medical device. In this way, a lower cost sensor for medical device connectors that enables detecting attached devices and identifying the attached devices based on dimensions of the ends of connectors of such devices may be provided.

Non-limiting embodiments or aspects of the present disclosure are directed to systems, methods, and computer program products that detect, with a sensor surrounding a connector of a medical device, a dimension of an end of another connector of another medical device when the another connector of the another medical device is connected to the connector of the medical device; and determine a type of the another medical device based on the detected dimension. In this way, devices may be identified without using communications between devices, readers, and/or tags and/or without relying on RFID tags or barcodes to provide identification numbers of the devices.

Referring to FIG. 1, non-limiting embodiments or aspects of an environment 100 in which systems, devices, products, apparatus, and/or methods, as described herein, may be implemented is shown. As shown in FIG. 1, environment 100 may include medical device 102, another medical device 104, sensor assembly 106, communication network 108, and/or remote computing device 110.

Medical device 102 and another medical device 104 may be configured to physically connect to each other as described in more detail herein. In some non-limiting embodiments or aspects, a medical device (e.g., medical device 102, another medical device 104, etc.) may include a syringe, a catheter, a disinfecting cap, and/or the like. For example, a type of a medical device may include at least one of: a syringe, a syringe size, catheter, a disinfecting cap, or any combination thereof. Further details regarding non-limiting embodiments or aspects of a medical device are provided below with regard to FIG. 3.

Sensor assembly 106 may be attached to (e.g., removably attached to, permanently attached to, etc.) or integrally formed with medical device 102 as described in more detail herein. Sensor assembly 106 may include may include one or more devices capable of receiving information and/or data from remote computing device 110 and/or another sensor assembly 106 (e.g., via communication network 108, etc.) and/or communicating information and/or data to remote computing device 110 and/or another sensor assembly 106 (e.g., via communication network 108, etc.). In some non-limiting embodiments or aspects, sensor assembly 106 includes one or more computing devices, chips, contactless transmitters, contactless transceivers, NFC transmitters, RFID transmitters, contact based transmitters, and/or the like. In some non-limiting embodiments or aspects, sensor assembly 106 can include one or more devices capable of transmitting information to remote computing system 110 and/or another sensor assembly 106 via a short range wireless communication connection (e.g., a communication connection that uses NFC protocol, a communication connection that uses Radio-frequency identification (RFID), a communication connection that uses a Bluetooth® wireless technology standard, and/or the like). In some non-limiting embodiments or aspects, sensor assembly 106 includes an integrated power source (not shown), such as a battery, and/or the like. In some non-limiting embodiments or aspects, sensor assembly 106 receives power via a wirelessly transmitted power source, such as via an RF transmission from another sensor assembly 106 and/or remote computing device 110, and/or the like. Further details regarding non-limiting embodiments or aspects of sensor assembly 106 are provided below with regard to FIGS. 3-8.

Communication network 108 may include one or more wired and/or wireless networks. For example, communication network 108 may include a cellular network (e.g., a long-term evolution (LTE) network, a third generation (3G) network, a fourth generation (4G) network, a fifth generation network (5G) network, a code division multiple access (CDMA) network, etc.), a public land mobile network (PLMN), a local area network (LAN), a wide area network (WAN), a metropolitan area network (MAN), a telephone network (e.g., the public switched telephone network (PSTN)), a private network, an ad hoc network, an intranet, the Internet, a fiber optic-based network, a cloud computing network, and/or the like, and/or a combination of these or other types of networks.

Remote computing device 110 may include one or more devices capable of receiving information and/or data from sensor assembly 106 and/or another remote computing network 110 (e.g., via communication network 108, etc.) and/or communicating information and/or data to sensor assembly 106 and/or another remote computing network 110 (e.g., via communication network 108, etc.). For example, remote computing device 110 may include a computing device, a server, a group of servers, a mobile device, a group of mobile devices, and/or the like. In some non-limiting embodiments or aspects, remote computing device 110 includes one or more computing devices, chips, contactless transmitters, contactless transceivers, NFC transmitters, RFID transmitters, contact based transmitters, and/or the like that enables remote computing device 110 to receive information directly from and/or communicate information directly to sensor assembly 106 via a short range wireless communication connection (e.g., a communication connection that uses NFC protocol, a communication connection that uses Radio-frequency identification (RFID), a communication connection that uses a Bluetooth® wireless technology standard, and/or the like). In some non-limiting embodiments or aspects, remote computing device 110 may be implemented within sensor assembly 106. In some non-limiting embodiments or aspects, remote computing device 110 is configured as a bedside unit that is capable of being located in a vicinity of a patient. For example, the bedside unit can be connected to a wall of a room of the patient, an IV pole, and/or a carrier held in place by a bed of the patient (e.g., between mattresses) near a side of the patient or the bed. The bedside device can display audio and/or visual warnings and/or indications, as described in more detail herein.

The number and arrangement of devices and systems shown in FIG. 1 is provided as an example. There may be additional devices and/or systems, fewer devices and/or systems, different devices and/or systems, or differently arranged devices and/or systems than those shown in FIG. 1. Furthermore, two or more devices and/or systems shown in FIG. 1 may be implemented within a single device and/or system, or a single device and/or system shown in FIG. 1 may be implemented as multiple, distributed devices and/or systems. Additionally, or alternatively, a set of devices and/or systems (e.g., one or more devices or systems) of environment 100 may perform one or more functions described as being performed by another set of devices and/or systems of environment 100.

Figure 2:
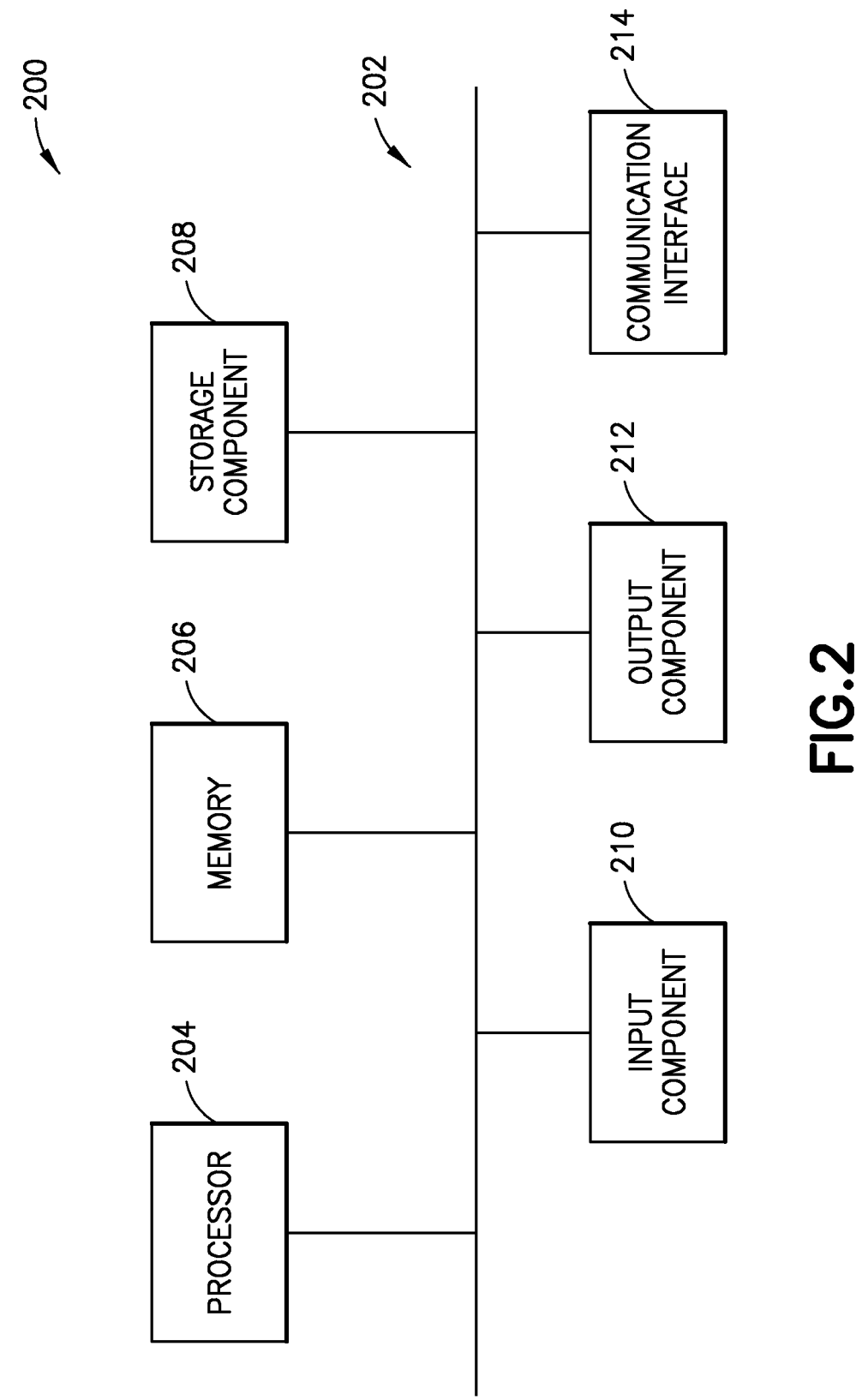
FIG. 2 is a diagram of non-limiting embodiments or aspects of components of one or more devices and/or one or more systems of FIG. 1.

Referring now to FIG. 2, FIG. 2 is a diagram of example components of a device 200. Device 200 may correspond to sensor assembly 106 and/or remote computing device 110. In some non-limiting embodiments or aspects, sensor assembly 106 and/or remote computing device 110 may include at least one device 200 and/or at least one component of device 200. As shown in FIG. 2, device 200 may include bus 202, processor 204, memory 206, storage component 208, input component 210, output component 212, and/or communication interface 214.

Bus 202 may include a component that permits communication among the components of device 200. In some non-limiting embodiments or aspects, processor 204 may be implemented in hardware, firmware, or a combination of hardware and software. For example, processor 204 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.), and/or the like, which can be programmed to perform a function. Memory 206 may include a random-access memory (RAM), a read only memory (ROM), and/or another type of dynamic or static storage device (e.g., a flash memory, a magnetic memory, an optical memory, etc.) that stores information and/or instructions for use by processor 204.

Storage component 208 may store information and/or software related to the operation and use of device 200. For example, storage component 208 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 210 may include a component that permits device 200 to receive information, such as via user input (e.g., a touch screen display, a keyboard, a keypad, a mouse, a button, a switch, a microphone, etc.). Additionally, or alternatively, input component 210 may include a sensor for sensing information (e.g., a global positioning system (GPS) component, an accelerometer, a gyroscope, an actuator, etc.). Output component 212 may include a component that provides output information from device 200 (e.g., a display, a speaker, one or more light-emitting diodes (LEDs), etc.).

Communication interface 214 may include a transceiver-like component (e.g., a transceiver, a separate receiver and transmission source, etc.) that enables device 200 to communicate with other devices, such as via a wired connection, a wireless connection, or a combination of wired and wireless connections. Communication interface 214 may permit device 200 to receive information from another device and/or provide information to another device. For example, communication interface 214 may include an Ethernet interface, an optical interface, a coaxial interface, an infrared interface, a radio frequency (RF) interface, a universal serial bus (USB) interface, a Wi-Fi interface, a cellular network interface, and/or the like.

Device 200 may perform one or more processes described herein. Device 200 may perform these processes based on processor 204 executing software instructions stored by a computer-readable medium, such as memory 206 and/or storage component 208. A computer-readable medium (e.g., a non-transitory computer-readable medium) is defined herein as a non-transitory memory device. A memory device includes memory space located inside of a single physical storage device or memory space spread across multiple physical storage devices.

Software instructions may be read into memory 206 and/or storage component 208 from another computer-readable medium or from another device via communication interface 214. When executed, software instructions stored in memory 206 and/or storage component 208 may cause processor 204 to perform one or more processes described herein. Additionally, or alternatively, hardwired circuitry may be used in place of or in combination with software instructions to perform one or more processes described herein. Thus, embodiments or aspects described herein are not limited to any specific combination of hardware circuitry and software.

Memory 206 and/or storage component 208 may include data storage or one or more data structures (e.g., a database, etc.). Device 200 may be capable of receiving information from, storing information in, communicating information to, or searching information stored in the data storage or one or more data structures in memory 206 and/or storage component 208.

The number and arrangement of components shown in FIG. 2 are provided as an example. In some non-limiting embodiments or aspects, device 200 may include additional components, fewer components, different components, or differently arranged components than those shown in FIG. 2. Additionally, or alternatively, a set of components (e.g., one or more components) of device 200 may perform one or more functions described as being performed by another set of components of device 200.

Figure 3:
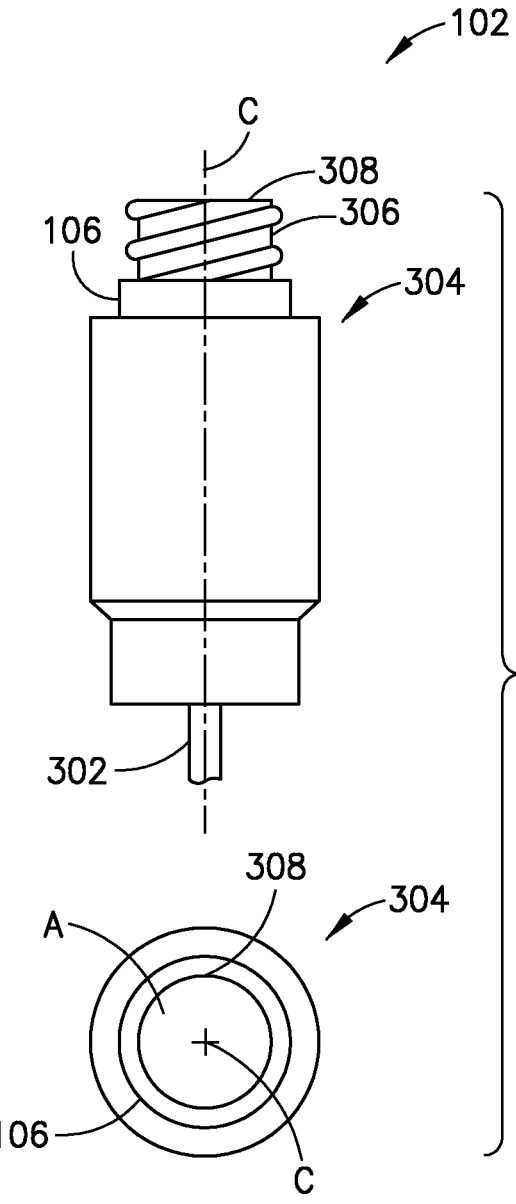
FIG. 3 is a diagram of non-limiting embodiments or aspects of components of one or more devices of FIG. 1.

Referring now to FIG. 3, FIG. 3 is a diagram of example components of medical device 102 (and/or medical device 104). For example, medical device 102 may include body 302, connector 304, connector tip 306, and connector end 308. Connector end 308 may be located at a distal end of connector tip 306 of connector 304 opposite of connector body 302. A center C of connector 304 (e.g., a center C of a cross sectional area A defined by connector end 308, etc.) may correspond to the longitudinal axis of connector 304. Additionally or alternatively, in a case of a sensor assembly 106 that completely surrounds connector 304 of medical device 102, a center C of sensor assembly 106 (e.g., a center C of a cross sectional area A defined by a distal end of sensor assembly 106, etc.) may correspond to the longitudinal axis of sensor assembly 106 and/or connector 304. Connector 304 of medical device 102 may be configured to physically connect (e.g., mate, attach, lock, press-fit, etc.) to a complementary connector 304 of another medical device 104. In some non-limiting embodiments or aspects, connector 304 includes a needleless connector (e.g., the BD MaxZero™ connector, etc.), a Luer connector, a catheter end connection, and/or the like.

As further shown in FIG. 3, sensor assembly 106 may surround connector 304 of medical device 102. For example, sensor assembly 106 may surround connector 304 of medical device 102 at connector tip 306 (e.g., at a distal end of connector 304 proximate connector end 308). In some non-limiting embodiments or aspects, sensor assembly 106 may completely surround connector 304 of medical device 102. For example, sensor assembly 106 may have a ring shape as shown in FIG. 3. In some non-limiting embodiments or aspects, sensor assembly 106 may only partially surround connector 304 of medical device 102. For example, sensor assembly 106 may have a C-shape. In some non-limiting embodiments or aspects, sensor assembly 106 may be removably attached to connector 304 (e.g., removably attached to connector tip 306, etc.). In some non-limiting embodiments or aspects, sensor assembly 106 may be integrally formed with connector 304 (e.g., integrally formed with connector tip 306, etc.).

The number and arrangement of components shown in FIG. 3 are provided as an example. In some non-limiting embodiments or aspects, medical device 102 (and/or medical device 104) may include additional components, fewer components, different components, or differently arranged components than those shown in FIG. 3.

Figure 4:
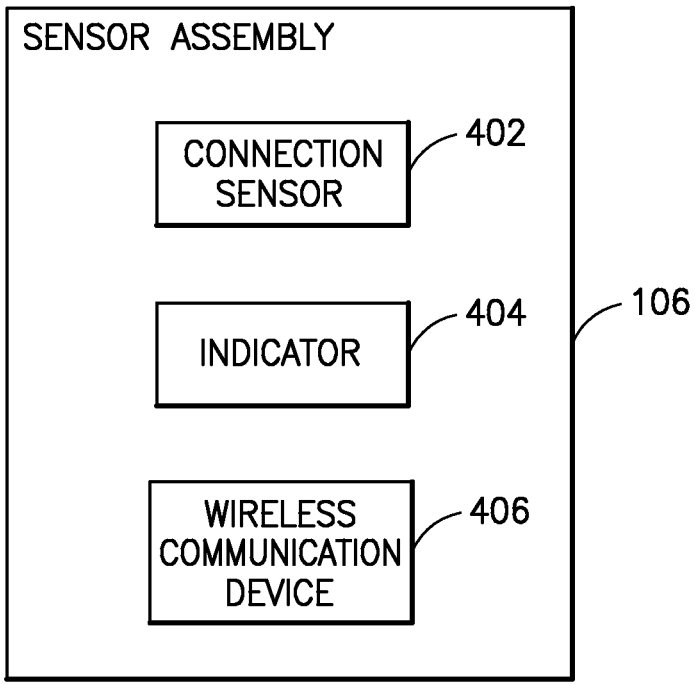
FIG. 4 is a diagram of non-limiting embodiments or aspects of components of one or more devices of FIG. 1.

Referring now to FIG. 4, FIG. 4 is a diagram of example components of sensor assembly 106. Sensor assembly 106 may include connection sensor 402, indicator 404, and/or wireless communication device 406.

Connection sensor 402 may be configured to detect a dimension of an end of another connector 304 of another medical device 104 when the another connector 304 of the another medical device 104 is connected to connector 304 of medical device 102. For example, the detected dimension may include at least one of (i) a distance of an outer edge of end 308 of the another connector 304 of the another medical device 104 from the center C of the connector 304 of medical device 104 and (ii) the cross sectional area A of the end 308 of the another connector 304 of the another medical device 104. In some non-limiting embodiments or aspects, connection sensor 402 may be configured to detect a connection and/or a disconnection of medical device 102 from another medical device 104. In some non-limiting embodiments or aspects, connection sensor 402 may include a force sensor and/or an optical sensor.

Indicator 404 may be configured to provide at least one of an audio indication and a visual indication associated with the dimension of the end 308 of the another connector 304 of the another medical device 104. For example, indicator 404 may include an LED, a vibrating element, a speaker, and/or the like. As an example, indicator 404 may output different colors of LED light and/or different sounds to indicate different dimensions or types of the another medical device 104. In such an example, a first output of indicator 404 (e.g., a blue light, etc.) may correspond to a first type of medical device (e.g., a syringe, a particular syringe size, etc.) associated with the detected dimension, a second output of indicator 404 (e.g., a green light, etc.) may correspond to a second type of medical device different than the first type of medical device (e.g., a disinfecting cap, a different sized syringe, etc.) associated with the detected dimension, and/or an nth output of indicator 404 (e.g., a red light, etc.) may correspond to an nth type of medical device different than the first type and second types of medical device (e.g., a catheter, a further different sized syringe, etc.) associated with the detected dimension.

Wireless communication device 406 may be configured to communicate information associated with the dimension of the end 308 of the another connector 306 of the another medical device 104 (and/or the type of the another medical device 104) to remote computing device 110. For example, wireless communication device 406 may communicate an indication of the dimension of the end 308 of the another connector 306 of the another medical device 104 and/or an indication of a type of the another medical device 104. As an example, wireless communication device 406 may communicate an indication of a connection of another medical device 104 to medical device 102 and/or a time associated therewith and/or an indication of a disconnection of another medical device 104 from medical device 102 and/or a time associated therewith. In some non-limiting embodiments, wireless communication device 406 is configured to communicate the information continuously, periodically, and/or in response to at least one of the following: receiving a polling signal from remote computing device 110 and/or another sensor assembly 106, actuation of connection sensor 402, or any combination thereof.

In some non-limiting embodiments or aspects, connection sensor 402, indicator 404, and/or wireless communication device 406 are sealed from the environment and/or self-contained. For example, connection sensor 402, indicator 404, and/or wireless communication device 406 may be sealed within and/or integrally formed within a water-impermeable coating (e.g., within a polyimide washer, etc.). In some non-limiting embodiments or aspects, connection sensor 402, indicator 404, and/or wireless communication device 406 are sealed within and/or integrally formed within medical device 102.

The number and arrangement of components shown in FIG. 4 are provided as an example. In some non-limiting embodiments or aspects, sensor assembly 106 may include additional components, fewer components, different components, or differently arranged components than those shown in FIG. 4. Additionally, or alternatively, a set of components (e.g., one or more components) of sensor assembly 106 may perform one or more functions described as being performed by another set of components of device 106.

Figure 5:
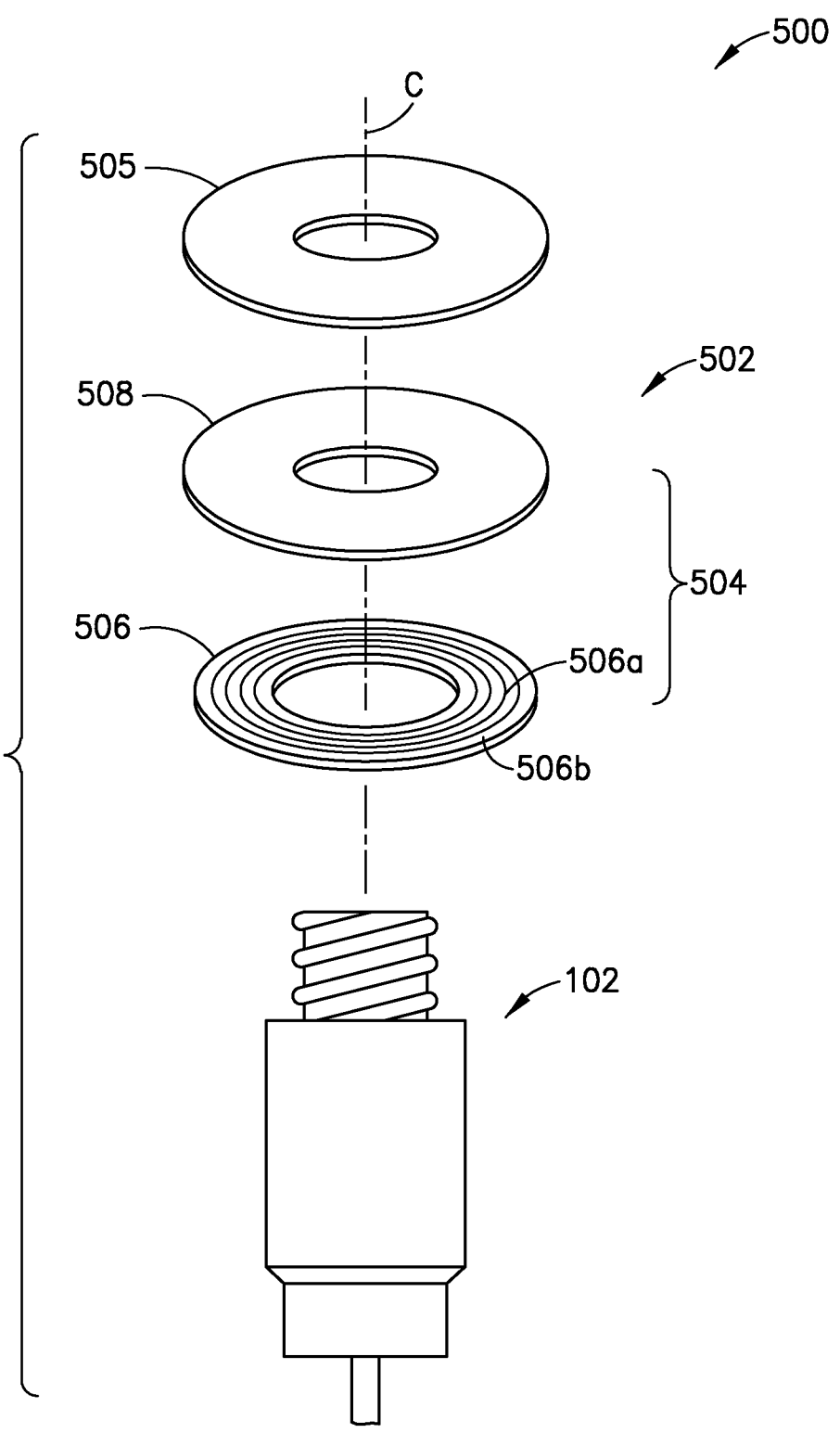
FIG. 5 is an exploded perspective view of an implementation of non-limiting embodiments or aspects of components of one or more devices of FIG. 4.

FIG. 5 is an exploded perspective view of a non-limiting embodiment or aspect of an implementation 500 relating to sensor assembly 106 shown in FIGS. 1, 3, and 4. In some non-limiting embodiments or aspects, sensor assembly 500 may be the same as or similar to sensor assembly 106. As shown in FIG. 5, sensor assembly 500 may include a force sensor 502. Force sensor 502 may include a plurality of switches 504 and/or a water impermeable coating 505. The plurality of switches 504 may be arranged at different distances from the center C of connector 304 of medical device 102. Each switch of the plurality of switches 504 may be configured to be actuated in response to a physical force applied to that switch to connect and/or break a flow of electricity through that switch.

The plurality of switches 504 may include a plurality of conductive circuits 506 surrounding connector 304 of medical device 102. For example, as shown in FIG. 5, the plurality of conductive circuits may include a plurality of concentric rings 506*a* (e.g., copper rings, etc.) on a flexible circuit board 506*b*.

The plurality of switches 504 may include a flexible layer of conductive or semi-conductive material 508 on the plurality of conductive circuits 506. For example, the flexible layer of conductive or semi-conductive material 508 may include a force-sensing resistor or a carbon and/or graphite infused polymer. In some non-limiting embodiments or aspects, the flexible layer of conductive or semi-conductive material 508 may include a flexible copper layer, a flexible silver powder coating, and/or the like. The flexible layer of conductive or semi-conductive material 508 may, in response to a physical pressure applied thereto, open or close one or more of the plurality of conductive circuits 506 to actuate one or more of the plurality of switches 504 to connect or break a flow of electricity through those switches. For example, application of a physical pressure to the flexible layer of conductive or semi-conductive material 508 above (e.g., immediately above, etc.) a conductive circuit 506 may actuate a switch 504 corresponding to that conductive circuit 506, whereas a lack of a physical pressure applied to the flexible layer of conductive or semi-conductive material 508 above the conductive circuit 506 may not actuate the switch 504 corresponding to that conductive circuit 506. As an example, the plurality of conductive circuits 506 arranged at different distances from the center C of connector 304 of medical device 102 (e.g., as concentric ring circuits, etc.) enable the flexible layer of conductive or semi-conductive material 508 to open or close different ones of those conductive circuits 506 in response to the application of a physical pressure from ends 308 of connectors 304 of another medical devices 104 having different dimensions (e.g., different distances of outer edges of the ends 308 of another connectors 304 of another medical devices 104 from the center C of the connector 304 of medical device 104, different cross sectional areas A of ends 308 of another connectors 304 of another medical devices 104, etc.). In such an example, actuation of a furthest switch of the plurality of switches 504 from the center C of the connector 304 of the medical device 102 may be associated with the dimension of the end 308 of the another connector 304 of the another medical device 104.

Figure 6:
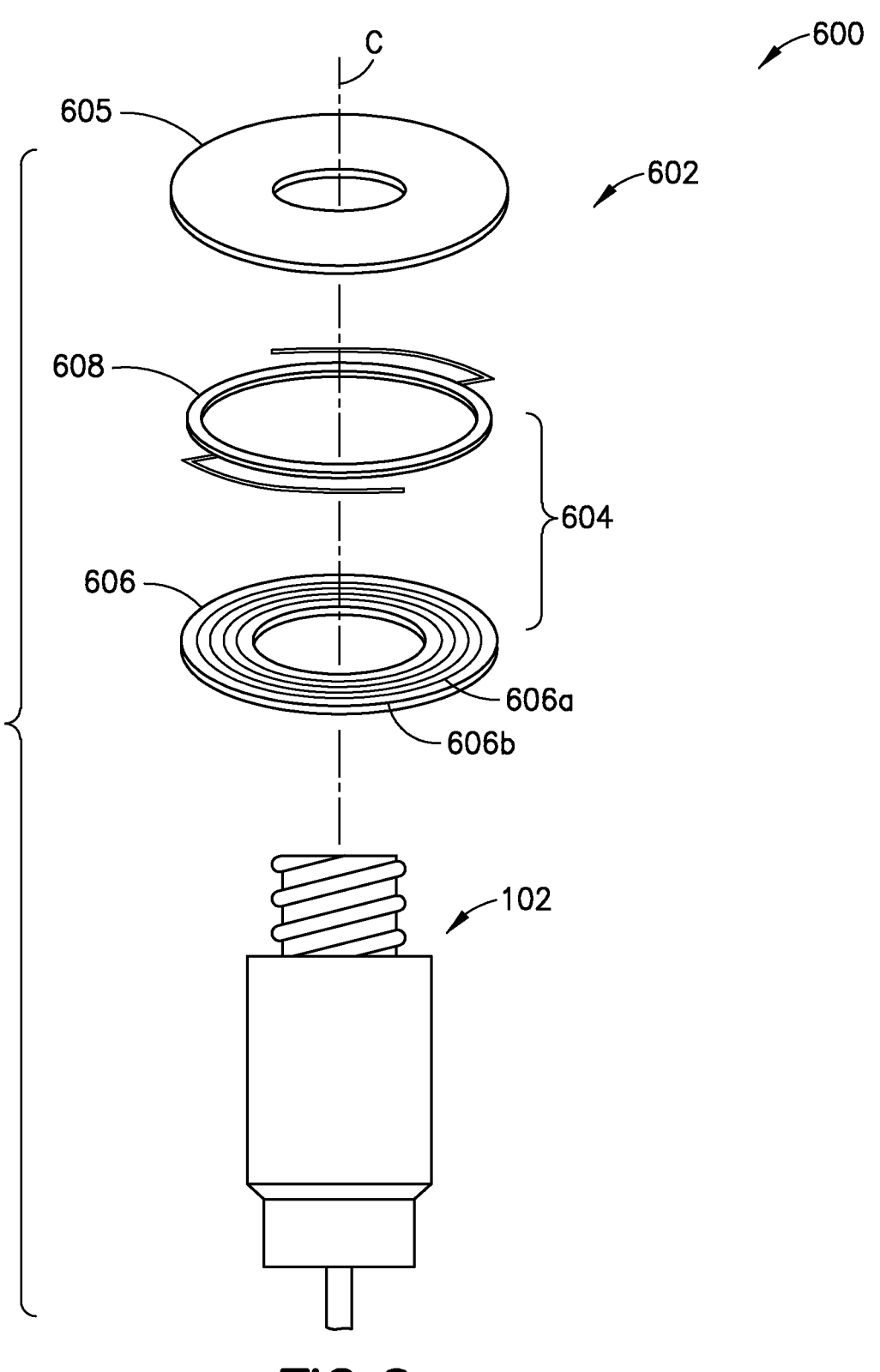
FIG. 6 is an exploded perspective view of an implementation of non-limiting embodiments or aspects of components of one or more devices of FIG. 4.

FIG. 6 is an exploded perspective view of a non-limiting embodiment or aspect of an implementation 600 relating to sensor assembly 106 shown in FIGS. 1, 3, and 4. In some non-limiting embodiments or aspects, sensor assembly 600 may be the same as or similar to sensor assembly 106. As shown in FIG. 6, sensor assembly 600 may include a force sensor 602. Force sensor 602 may include a plurality of switches 604 and/or a water impermeable coating 605. The plurality of switches 604 may be arranged at different distances from the center C of connector 304 of medical device 102. Each switch of the plurality of switches 604 may be configured to be actuated in response to a physical force applied to that switch to connect and/or break a flow of electricity through that switch.

The plurality of switches 604 may include a plurality of conductive circuits 606 surrounding connector 304 of medical device 102. For example, as shown in FIG. 6, the plurality of conductive circuits may include a plurality of concentric rings 606*a* (e.g., copper rings, etc.) on a flexible circuit board 606*b*.

The plurality of switches 604 may include one or more spring loaded metallic rings 608 on the plurality of conductive circuits. The one or more spring loaded metallic rings 608 may, in response to a physical pressure applied thereto, open or close one or more of the plurality of conductive circuits 606 to actuate one or more of the plurality of switches 604 to connect or break a flow of electricity through those switches. For example, application of a physical pressure to a spring loaded metallic ring 608 above (e.g., immediately above, etc.) a conductive circuit 506 may actuate a switch 504 corresponding to that conductive circuit 506, whereas a lack of a physical pressure applied to a spring loaded metallic ring 608 above the conductive circuit 506 may not actuate the switch 504 corresponding to that conductive circuit 506. As an example, the plurality of conductive circuits 506 arranged at different distances from the center C of connector 304 of medical device 102 (e.g., as concentric ring circuits, etc.) enable one or more spring loaded metallic rings 608 to open or close different ones of those conductive circuits 506 in response to the application of a physical pressure from ends 308 of connectors 304 of another medical devices 104 having different dimensions (e.g., different distances of outer edges of ends 308 of another connectors 304 of another medical devices 104 from the center C of the connector 304 of medical device 104, different cross sectional areas A of ends 308 of another connectors 304 of another medical devices 104, etc.). In such an example, actuation of a furthest switch of the plurality of switches 504 from the center C of the connector 304 of the medical device 102 may be associated with the dimension of the end 308 of the another connector 304 of the another medical device 104.

Figure 7:
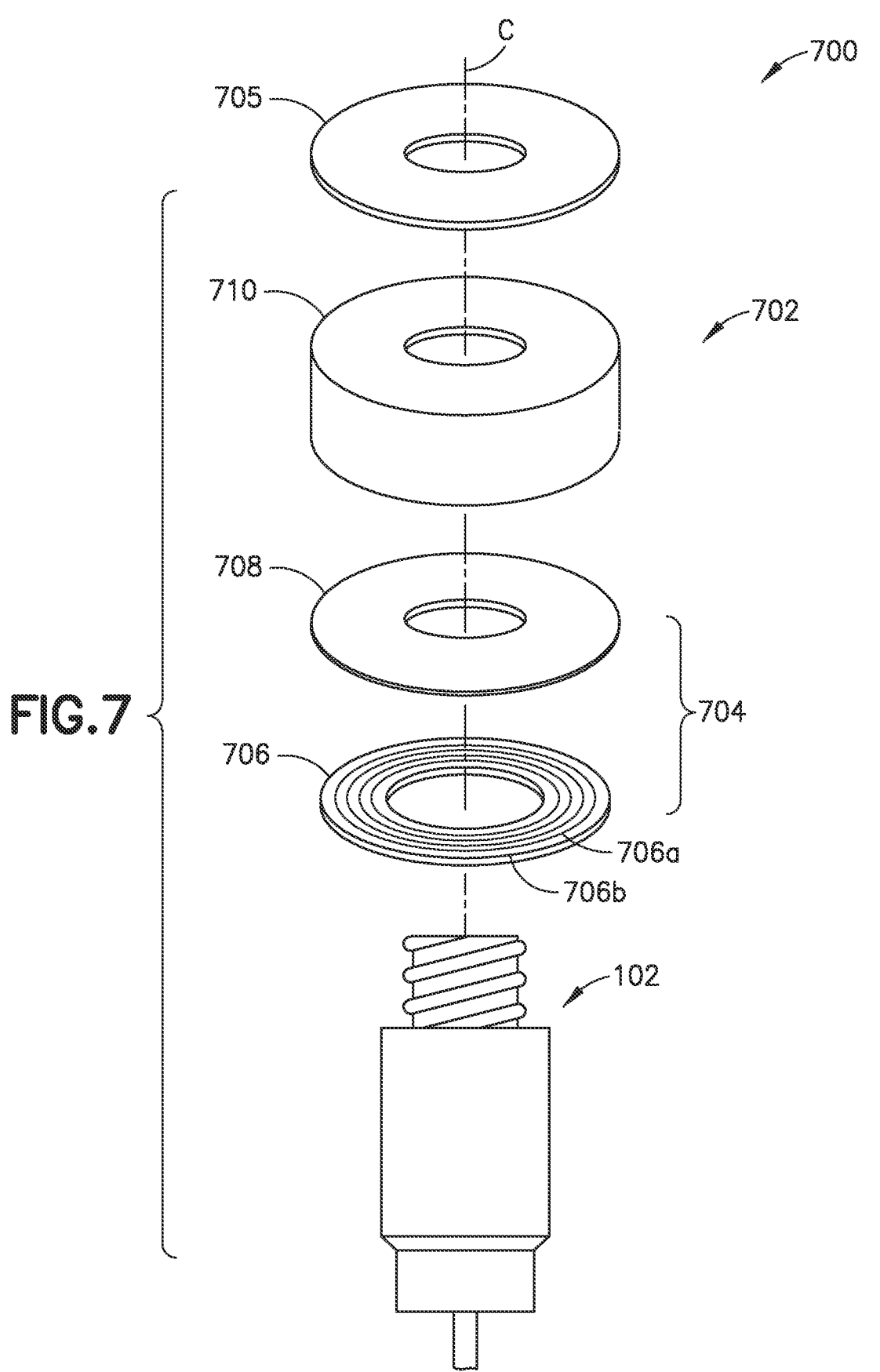
FIG. 7 is an exploded perspective view of an implementation of non-limiting embodiments or aspects of components of one or more devices of FIG. 4.

FIG. 7 is an exploded perspective view of a non-limiting embodiment or aspect of an implementation 700 relating to sensor assembly 106 shown in FIGS. 1, 3, and 4. In some non-limiting embodiments or aspects, sensor assembly 700 may be the same as or similar to sensor assembly 106. As shown in FIG. 7, sensor assembly 700 may include a force sensor 702. Force sensor 702 may include a plurality of switches 704 and/or a water impermeable coating 705. The plurality of switches 704 may include a plurality of conductive circuits 706 surrounding connector 304 of medical device 102. The plurality of switches 704 may include a flexible layer 708 on the plurality of conductive circuits 706 (e.g., a flexible layer of conductive or semi-conductive material on the plurality of conductive circuits 706, one or more spring loaded metallic rings on the plurality of conductive circuits 706, etc.). In some non-limiting embodiments or aspects, force sensor 702 may be the same as or similar to force sensor 502 or force sensor 602. In some non-limiting embodiments or aspects, the plurality of switches 704 may be the same as or similar to the plurality of switches 502 or the plurality of switches 602. In some non-limiting embodiments or aspects, water impermeable coating 705 may be the same as or similar to water impermeable coating 505 or water impermeable coating 605. In some non-limiting embodiments or aspects, the plurality of conductive circuits 706 may be the same as or similar to the plurality of conductive circuits 506 or the plurality of conductive circuits 606. In some non-limiting embodiments or aspects, flexible layer 708 may be the same as or similar to flexible layer of conductive or semi-conductive material 508 on the plurality of conductive circuits 706, one or more spring loaded metallic rings 608 on the plurality of conductive circuits 706.

As shown in FIG. 7, force sensor 702 may include a layer of anisotropic elastic material 710 on flexible layer 708. For example, the layer of anisotropic elastic material 710 may have an orientation of stress transmission such that a force applied to the layer of anisotropic elastic material 710 in a direction along the longitudinal axis of medical device 102 is transmitted by the layer of anisotropic elastic material 710 to flexible layer 708, which may enable a physical force to be transmitted through a distance to flexible layer 708. As an example, the layer of anisotropic elastic material 710 may include an extruded material including polymer chains oriented parallel to the longitudinal axis of medical device 102 (e.g., oriented along an axis orthogonal to a distal surface of flexible layer 708). In such an example, the layer of anisotropic elastic material 710 may protect the flexible layer 708 when devices are attached to medical device 102 and transmit forces uniaxially from the attached devices to appropriate portions of the flexible layer 708. For example, preferred material properties may be such that when an device of certain geometry and cross section is attached to the needleless connector, the layer of anisotropic elastic material 710 faithfully transmits the approximate pressure distribution, which is impressed on the flexible layer 708.

Figure 8:
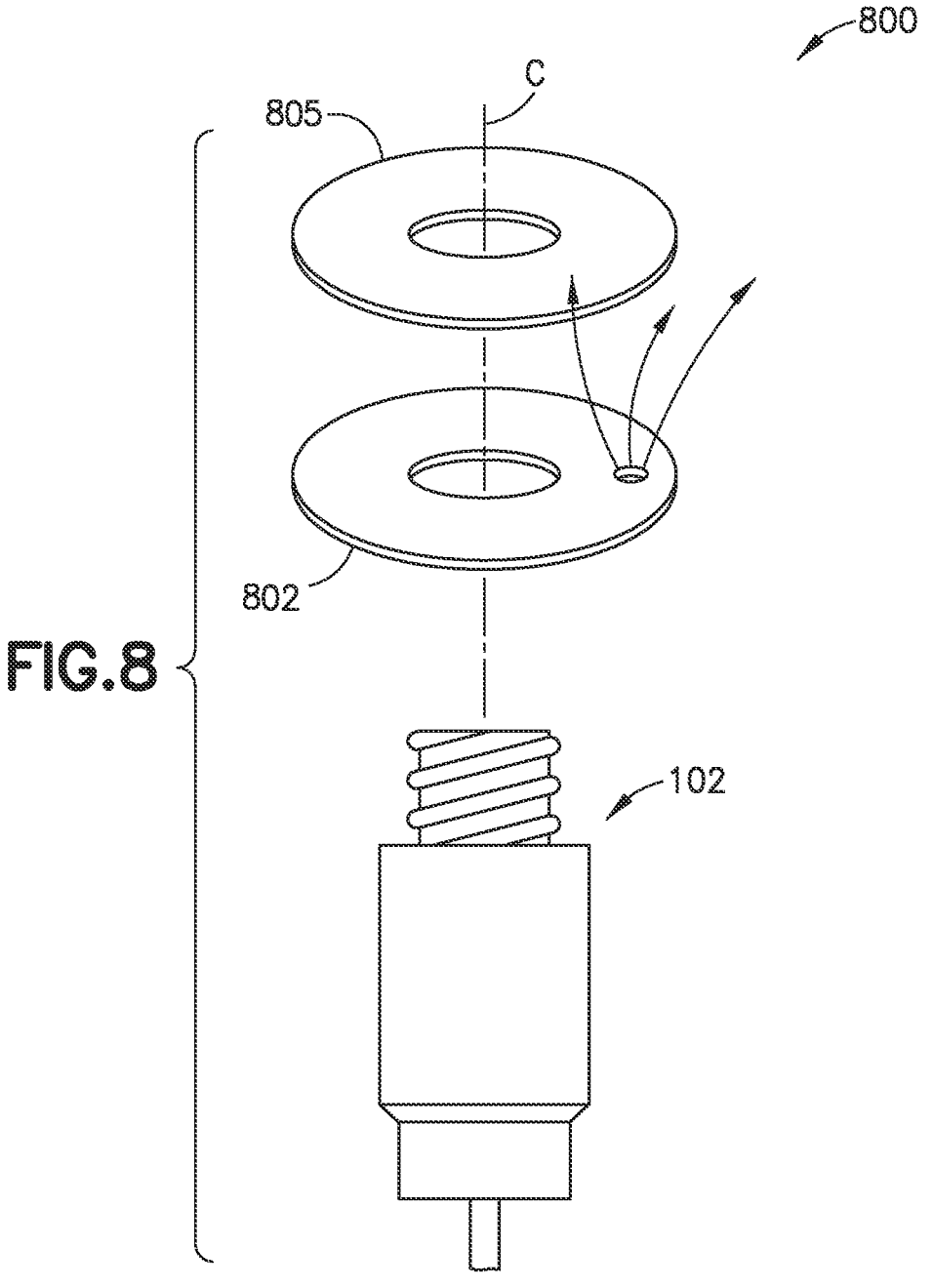
FIG. 8 is an exploded perspective view of an implementation of a non-limiting embodiment or aspect of components of one or more devices of FIG. 4.

FIG. 8 is an exploded perspective view of a non-limiting embodiment or aspect of an implementation 800 relating to sensor assembly 106 shown in FIGS. 1, 3, and 4. In some non-limiting embodiments or aspects, sensor assembly 800 may be the same as or similar to sensor assembly 106. As shown in FIG. 8, sensor assembly 800 may include an optical sensor 802 and/or a water impermeable coating 805. For example, optical sensor 802 may be configured to detect at least one of (i) a distance of an outer edge of the end of the another connector of the another medical device from a center of the connector of the medical device and (ii) a cross sectional area of the end of the another connector of the another medical device. As an example, optical sensor 802 may detect attachment of objects of interest based on reflection of an interrogation optical beam from the object of interest. As an example, optical sensor 802 may include a light sensor, a camera, a color sensor, and/or the like. In some non-limiting embodiments or aspects, sensor assembly 106 may include optical sensor 802 and force sensor 502, 602, or 702.

Figure 9:
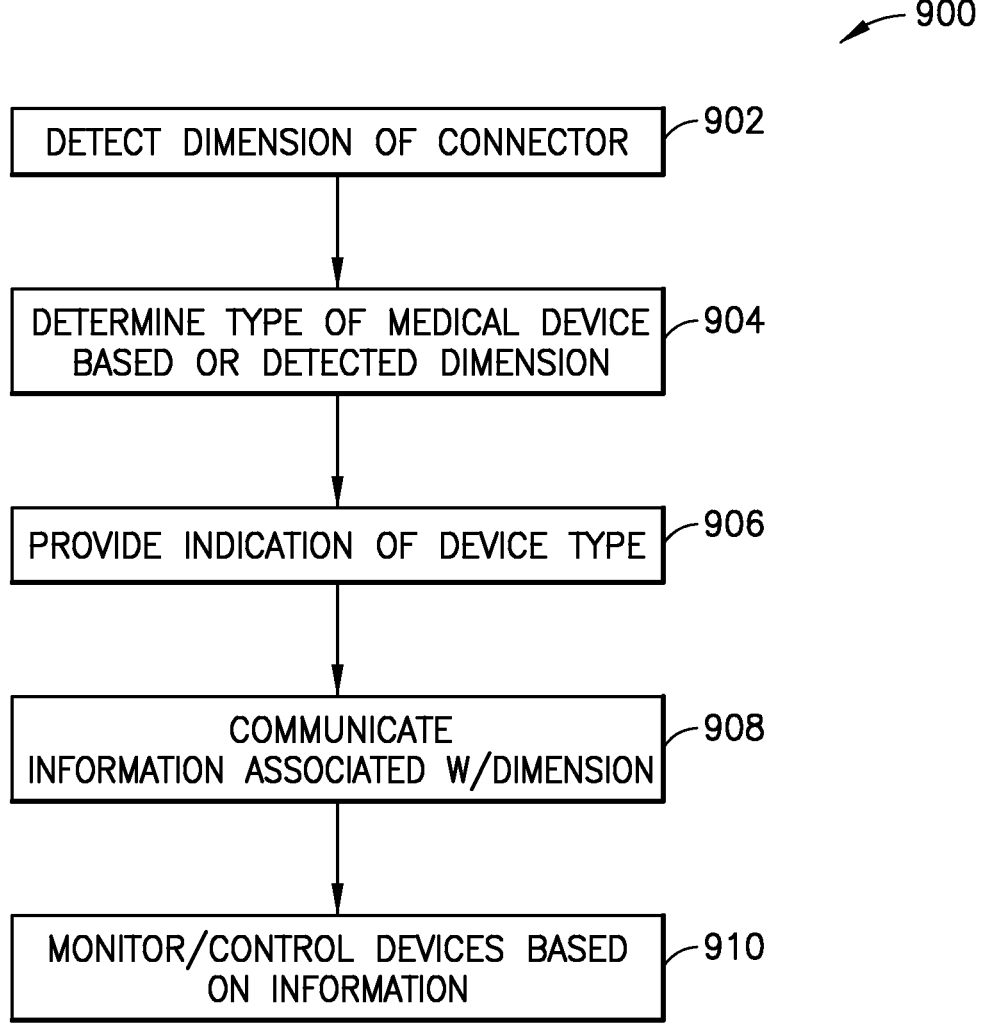
FIG. 9 is a flowchart of non-limiting embodiments or aspects of a process for identifying devices connected to device connectors.

Referring now to FIG. 9, a process 900 is shown for identifying device connections in a connection area. In some non-limiting embodiments or aspects, one or more of the steps of process 900 may be performed (e.g., completely, partially, etc.) by sensor assembly 106 and/or remote computing device 110.

As shown in FIG. 9, at step 902, process 900 includes detecting a dimension of an end of a connector of a medical device. For example, sensor assembly 106 may detect a dimension of an end of a connector of a medical device. As an example, sensor assembly 106 may detect, with connection sensor 402 surrounding connector 304 of medical device 102, a dimension of an end 308 of another connector 304 of another medical device 104 when the another connector 304 of the another medical device 104 is connected to the connector 304 of the medical device 102 (e.g., when the another connector 304 of the another medical device 104 is connected to the connector 304 of the medical device 102, when the another connector 304 of the another medical device 104 is being connected to the connector 304 of the medical device 102, etc.).

As shown in FIG. 9, at step 904, process 900 includes determining a type of medical device based on a detected dimension. For example, sensor assembly 106 and/or remote computing device 110 may determine a type of medical device based on a detected dimension. As an example, sensor assembly 106 and/or remote computing device 110 may determine a type of the another medical device 104 based on the detected dimension. In such an example, sensor assembly 106 and/or remote computing device 110 may access a look-up table that correlates dimensions of ends 308 of connectors 304 of medical devices 102, 104 (e.g., distances of outer edges of the ends of connectors of medical devices from a center of the connector of the medical device, cross sectional areas of ends of connectors of medical devices, one or more actuated switches, etc.) to types of medical devices associated with those dimensions.

As shown in FIG. 9, at step 906, process 900 includes providing an indication of a type of a medical device. For example, sensor assembly 106 and/or remote computing device 110 may provide an indication of a type of a medical device. As an example, sensor assembly 106 and/or remote computing device 110 may provide at least one of an audio indication and a visual indication associated with the dimension of the end of the another connector of the another medical device.

As shown in FIG. 9, at step 908, process 900 includes communicating information associated with a detected dimension. For example, sensor assembly 106 and/or remote computing device 110 may communicate information associated with a detected dimension. As an example, sensor assembly 106 and/or remote computing device 110 may communicate, with a wireless communication device, to a remote computing device 110, information associated with at least one of (i) the dimension of the end of the another connector of the another medical device and (ii) a connection or a disconnection of the medical device 102 to or from the another medical device 104. In such an example, the information associated with a detected dimension may indicate a connection state of medical device 102 and another medical device 104. For example, information can indicate a connected state, a disconnected state, a level of connection of between medical device 102 and another medical device 104, and/or a time associated therewith.

It is noted herein that in addition to the detection of various states of connection/disconnection, the system can also be utilized to monitor preparation and/or maintenance of a fluid path. For example, other events that can be captured include disinfection of a device of the system, capping/decapping of a device of the system, and monitoring placement of a device into or out of the system (such as monitoring placement of a catheter securement device). It is also contemplated herein that the system can detect additional disinfection processes, such as the preparation of an IV site with an antimicrobial agent.

As shown in FIG. 9, at step 910, process 900 includes monitoring and/or controlling one or more medical devices based on information associated with a detected dimension. For example, remote computing device 110 may monitor and/or control one or more medical devices based on information associated with a detected dimension.

In some non-limiting embodiments or aspects, remote computing device 110 may control a flow of a fluid in a fluid flow path including medical device 102 and another medical device 104 based on the information associated with the detected dimension. For example, remote computing device 110 can issue an alert and/or control one or more devices in the fluid flow path to stop the fluid flow and/or adjust the fluid flow, e.g., using one or more electronically controlled valves, based on the information associated with the detected dimension (e.g., in response to information indicating that medical device 102 and another medical device 104 in the fluid flow path have been disconnected, in response to information that an incompatible medical device 104 has been connected to medical device 102, etc.).

In some non-limiting embodiments or aspects, remote computing device 110 may receive a patient identifier associated with a patient, receive a medication identifier of a medication to be delivered to the patient via a fluid flow path including medical device 102 and/or another medical device 104, associate the patient identifier and the medication identifier with medical device 102 and/or another medical device 104 in the fluid flow path, and control the flow of the fluid in the fluid flow path based at least partially on the patient identifier, the medication identifier, and/or the information associated with the detected dimension. As an example, remote computing device 110 may determine at least one of the following: a connection state at a point of entry of a fluid flow path, a volume of fluid in the fluid flow path and/or at a point of entry based on a determined device type, a type of fluid or medication in the fluid flow path and/or at the point of entry, a flow rate of fluid in the fluid flow path and/or at a point of entry based on the determined device type and/or medication type, or any combination thereof. For example, remote computing device 110 may compare medication, medication dosage, medication delivery route, and/or medication delivery time determined based on the patient identifier, the medication identifier, and/or the information associated with the detected dimension to an approved patient, approved medication, approved medication dosage, approved medication delivery route, and/or approved medication delivery time associated with the patient identifier and/or the medication identifier to reduce medication administration errors. The remote computing device 110 can issue an alert and/or control one or more devices in the flow path to stop fluid flow and/or adjust fluid flow based on the patient identifier, the medication identifier, and/or the information associated with the detected dimension. For example, if a medication sensed at a point of entry in the fluid flow path is determined to be an improper medication for the patient, an improper dosage for the patient and/or medication, an improper medication delivery route for the patient and/or medication (e.g., improper point of entry to the fluid flow path), and/or an improper medication delivery time for the patient and/or medication, the remote computing device 110 can issue an alert and/or control one or more devices in the flow path to stop the fluid flow.

Although embodiments or aspects have been described in detail for the purpose of illustration and description, it is to be understood that such detail is solely for that purpose and that embodiments or aspects are not limited to the disclosed embodiments or aspects, but, on the contrary, are intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment or aspect. In fact, any of these features can be combined in ways not specifically recited in the claims and/or disclosed in the specification. Although each dependent claim listed below may directly depend on only one claim, the disclosure of possible implementations includes each dependent claim in combination with every other claim in the claim set.

What is claimed is:

1. A sensor assembly comprising:
   a sensor in communication with a connector of a medical device including a fluid flow path, wherein the sensor is configured to detect a dimension of an end of another connector of another medical device when the another connector of the another medical device is connected to the connector of the medical device, wherein the sensor is configured to detect a disconnection when the another connector of the another medical device is disconnected from the connector of the medical device, wherein the sensor includes a force sensor having a plurality of switches, and wherein each switch of the plurality of switches is configured to be actuated in response to a physical force applied to at least one of the connector and the sensor; and
   an indicator, for indicating information sensed from the sensor, wherein the sensor and the indicator are one of (i) sealed together within a water-impermeable coating that surrounds the connector of the medical device or (ii) sealed together within the connector of the medical device,
   wherein at least two of the plurality of switches are arranged at different distances from a longitudinal axis of the connector of the medical device.

2. The sensor assembly of claim 1, wherein the plurality of switches includes a plurality of conductive circuits surrounding the connector of the medical device.

3. The sensor assembly of claim 2, wherein the plurality of conductive circuits includes a plurality of concentric rings.

4. The sensor assembly of claim 2, wherein the plurality of switches includes a flexible layer of conductive or semi-conductive material on the plurality of conductive circuits.

5. The sensor assembly of claim 4, wherein the flexible layer of conductive or semi-conductive material includes a force-sensing resistor or a carbon and/or graphite infused polymer.

6. The sensor assembly of claim 4, wherein the water-impermeable coating surrounds the flexible layer and the plurality of conductive circuits.

7. The sensor assembly of claim 4, wherein the plurality of switches includes a layer of anisotropic elastic material on the flexible layer.

8. The sensor assembly of claim 2, wherein the plurality of switches includes a spring loaded metallic ring on the plurality of conductive circuits.

9. The sensor assembly of claim 1, wherein the sensor includes an optical sensor.

10. The sensor assembly of claim 1, wherein the connector includes a needless connector or a Luer connector.

11. The sensor assembly of claim 1, wherein the detected dimension includes at least one of (i) a distance of an outer edge of the end of the another connector of the another medical device from a longitudinal axis of the connector of the medical device and (ii) a cross sectional area of the end of the another connector of the another medical device.

12. The sensor assembly of claim 1, wherein the indicator comprises a speaker and one or more light-emitting diodes (LEDs), wherein the indicator is configured to provide at least one of an audio indication via the speaker and a visual indication via the one or more LEDs associated with the dimension of the end of the another connector of the another medical device.

13. The sensor assembly of claim 1, further comprising:
   a wireless communication device configured to communicate, to a remote computing device, information associated with at least one of (i) the dimension of the end of the another connector of the another medical device and (ii) a connection or a disconnection of the medical device to or from the another medical device,
   wherein the wireless communication device is the one of (i) sealed together with the indicator and the sensor within the water-impermeable coating that surrounds the connector of the medical device or (ii) sealed together with the indicator and the sensor within the connector of the medical device, with the indicator and the sensor.

14. The sensor assembly of claim 1, further comprising: one or more processors programmed and/or configured to determine a type of the another medical device based on the detected dimension.

15. A system comprising:
a sensor in communication with a connector of a medical device including a fluid flow path, wherein the sensor is configured to detect a dimension of an end of another connector of another medical device when the another connector of the another medical device is connected to the connector of the medical device and wherein the sensor is configured to detect a disconnection when the another connector of the another medical device is disconnected from the connector of the medical device; and
an indicator, for indicating information sensed from the sensor, wherein the sensor and the indicator are one of (i) sealed together within a water-impermeable coating that surrounds the connector of the medical device or (ii) sealed together within the connector of the medical device;
one or more processors programmed and/or configured to:
determine a type of the another medical device based on the detected dimension; and
provide an output associated with the detected dimension;
wherein the sensor includes a force sensor having a plurality of switches, wherein each switch of the plurality of switches is configured to be actuated in response to a physical force applied to at least one of the connector and the sensor, and
wherein at least two of the the plurality of switches are arranged at different distances from a longitudinal axis of the connector of the medical device.

16. The system of claim 15, wherein actuation of a furthest switch of the plurality of switches from the longitudinal axis of the connector of the medical device is associated with the dimension of the end of the another connector of the another medical device.

17. The system of claim 15, wherein the sensor includes an optical sensor, and wherein the detected dimension includes at least one of (i) a distance of an outer edge of the end of the another connector of the another medical device from a longitudinal axis of the connector of the medical device and (ii) a cross sectional area of the end of the another connector of the another medical device.

18. The system of claim 15, further comprising:
a wireless communication device configured to communicate, to the one or more processors, information associated with at least one of (i) the dimension of the end of the another connector of the another medical device and (ii) a connection or a disconnection of the medical device to or from the another medical device.

19. The system of claim 15, wherein the type of the another medical device includes a syringe, a catheter, or a disinfecting cap.

20. A method comprising:
detecting, with a sensor surrounding an exterior surface of a connector of a medical device including a fluid flow path, a dimension of an end of another connector of another medical device when the another connector of the another medical device is connected to the connector of the medical device;

determining, with at least one processor, a type of the another medical device based on the detected dimension;
providing, with an indicator, an output associated with the detected dimension, wherein the sensor and the indicator are one of (i) sealed together within a water-impermeable coating that surrounds the connector of the medical device or (ii) sealed together within the connector of the medical device; and
detecting, with the sensor surrounding the connector of the medical device, when the another connector of the another medical device is disconnected from the connector of the medical device;
wherein the sensor includes a force sensor having a plurality of switches, and wherein each switch of the plurality of switches is configured to be actuated in response to a physical force applied to at least one of the connector and the sensor, and
wherein at least two of the plurality of switches are arranged at different distances from a longitudinal axis of the connector of the medical device.

21. The method of claim 20, wherein detecting the dimension of the end of the another connector of the another medical device includes detecting at least one of (i) a distance of an outer edge of the end of the another connector of the another medical device from the longitudinal axis of the connector of the medical device and (ii) a cross sectional area of the end of the another connector of the another medical device.

22. The method of claim 20, further comprising:
communicating, with a wireless communication device, to a remote computing device, information associated with at least one of (i) the dimension of the end of the another connector of the another medical device and (ii) a connection or a disconnection of the medical device to or from the another medical device.

23. The method of claim 22, further comprising:
controlling, with at least one processor, a flow of a fluid in a fluid flow path including the medical device and the another medical device based on the information.

24. A computer program product comprising at least one non-transitory computer-readable medium including program instructions that, when executed by at least one processor, cause the at least on processor to:
control a sensor surrounding an exterior surface of a connector of a medical device including a fluid flow path to detect a dimension of an end of another connector of another medical device when the another connector of the another medical device is connected to the connector of the medical device;
determine a type of the another medical device based on the detected dimension;
control an indicator to provide an output associated with the detected dimension, wherein the sensor and the indicator are one of (i) sealed together within a water-impermeable coating that surrounds the connector of the medical device or (ii) sealed together within the connector of the medical device; and
control the sensor surrounding the connector of a medical device when the another connector of the another medical device is disconnected from the connector of the medical device;
wherein the sensor includes a force sensor having a plurality of switches, and wherein each switch of the plurality of switches is configured to be actuated in response to a physical force applied to at least one of the connector and the sensor, and wherein at least two of the plurality of switches are arranged at different distances from a longitudinal axis of the connector of the medical device.

\* \* \* \* \*